(12) United States Patent
Herold et al.

(10) Patent No.: US 8,680,079 B2
(45) Date of Patent: *Mar. 25, 2014

(54) TETRAHYDRO-IMIDAZO [1,5-A] PYRIDYIN DERIVATIVES AS ALDOSTERONE SYNTHASE INHIBITORS

(75) Inventors: Peter Herold, Basel (CH); Robert Mah, Muttenz (CH); Vincenzo Tschinke, Binningen (CH); Christoph Schumacher, Bettingen (CH); Michael Quirmbach, Basel (CH)

(73) Assignee: Novartis AG, Basel (CH)

( * ) Notice: Subject to any disclaimer, the term of this patent is extended or adjusted under 35 U.S.C. 154(b) by 1814 days.

This patent is subject to a terminal disclaimer.

(21) Appl. No.: 11/597,623

(22) PCT Filed: May 27, 2005

(86) PCT No.: PCT/EP2005/052419

§ 371 (c)(1),
(2), (4) Date: Nov. 27, 2006

(87) PCT Pub. No.: WO2005/118581

PCT Pub. Date: Dec. 15, 2005

(65) Prior Publication Data

US 2007/0225232 A1 Sep. 27, 2007

(30) Foreign Application Priority Data

May 28, 2004 (CH) .................................. 915/04

(51) Int. Cl.
| | | |
|---|---|---|
| *C07D 471/02* | (2006.01) | |
| *C07D 491/02* | (2006.01) | |
| *C07D 498/02* | (2006.01) | |
| *C07D 513/02* | (2006.01) | |
| *C07D 515/02* | (2006.01) | |
| *C07D 345/00* | (2006.01) | |
| *C07D 517/00* | (2006.01) | |

(52) U.S. Cl.
USPC ............................................. 514/119; 540/1

(58) Field of Classification Search
USPC ............................................. 546/119; 540/1
See application file for complete search history.

(56) References Cited

U.S. PATENT DOCUMENTS

| 4,617,307 A | 10/1986 | Browne |
| 4,889,861 A | 12/1989 | Browne |
| 5,057,521 A | 10/1991 | Häusler et al. |
| 7,612,088 B2 | 11/2009 | Herold et al. |
| 7,795,253 B2 | 9/2010 | Herold et al. |
| 7,799,780 B2 | 9/2010 | Herold et al. |
| 7,879,847 B2 | 2/2011 | Herold et al. |
| 2007/0208035 A1 | 9/2007 | Herold et al. |
| 2007/0225232 A1 | 9/2007 | Herold et al. |
| 2008/0076794 A1 | 3/2008 | Herold et al. |
| 2009/0012068 A1 | 1/2009 | Herold et al. |
| 2009/0048241 A1 | 2/2009 | Herold et al. |
| 2009/0192144 A1 | 7/2009 | Herold et al. |
| 2009/0192145 A1 | 7/2009 | Herold et al. |
| 2009/0192149 A1 | 7/2009 | Herold et al. |
| 2010/0010015 A1 | 1/2010 | Herold et al. |
| 2010/0168145 A1 | 7/2010 | Herold et al. |

FOREIGN PATENT DOCUMENTS

| EP | 0366609 | * 10/1989 | ............. A61K 31/44 |
| EP | 0 366 609 | 5/1990 | |
| JP | 63-145286 | 6/1988 | |
| JP | 9-71586 | * 3/1997 | ........... C07D 487/04 |
| WO | 97/00257 | 1/1997 | |

OTHER PUBLICATIONS

Lennart Hansson, et al, Randomized Trial of Old and New Antihypertensive Drugs in Elderly Patients: Cardiovascular Mortality and Morbidity the Swedish Trial in Old Patients with Hypertension-2 Study, 354 LANCET 1751 (Nov. 20, 1999).*
Machine Translation of Kawanami JP9-71586.*
Full Translation Kawanami JP 9-71586.*
Machine Translation of Kawanami JP9-71586 (Feb. 15, 2011).*
Full Translation of Kawanami JP9-71586 (Mar. 2011).*
Martyn C.R. Symons et al., "Electron Addition to Halogen Derivatives of Imidazoles", Tetrahedron Letters, vol. 30, No. 11, pp. 1409-1412, 1989.
Database WPI, Section CH, week 199721, Derwent Publications Ltd., London, GB, AN 1997-231178, XP002339566 & JP 09 071586, Mar. 18, 1997.
David Davey et al., "Cardiotonic Agents. 1. Novel 8-Aryl-Substituted Imidazo[1,2-a]and -[1,5-a]pyridines and Imidazo[1,5-a]pyridinones as Potential Positive Inotropic Agents", Journal of Medicinal Chemistry, 30(8), pp. 1337-1342, CODEN: JMCMAR; ISSN: 0022-2623, XP002339564, 1987.

* cited by examiner

*Primary Examiner* — Sean Basquill
(74) *Attorney, Agent, or Firm* — Wenderoth, Lind & Ponack, L.L.P.

(57) ABSTRACT

The application relates to novel heterocyclic compounds of the general formula (I) in which R, $R^1$, $R^2$, X, Y, Z and n have the meanings defined in the description, to a process for their preparation and to the use of these compounds as medicaments, in particular as aldosterone synthase inhibitors.

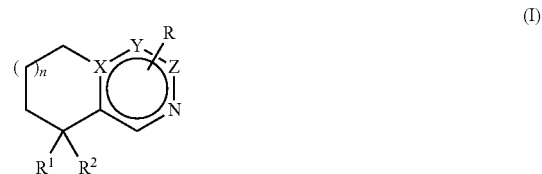

(I)

16 Claims, No Drawings

TETRAHYDRO-IMIDAZO [1,5-A] PYRIDYIN DERIVATIVES AS ALDOSTERONE SYNTHASE INHIBITORS

The invention relates to novel heterocyclic compounds, to a process for preparing the compounds, to pharmaceutical products containing them, and to their use as active pharmaceutical ingredients, in particular as aldosterone synthase inhibitors.

The present invention relates firstly to compounds of the general formula

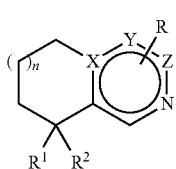

(I)

in which
X is N;
Y is C;
Z is a bond;
R a) is hydrogen; or
  b) is $C_1$-$C_8$alkyl, $C_1$-$C_8$-alkoxy, halogen or trifluoromethyl;
$R^1$ is $C_1$-$C_8$-alkyl, $C_2$-$C_8$-alkenyl, $C_2$-$C_8$-alkynyl, aryl-$C_0$-$C_4$-alkyl or unsaturated heterocyclyl-$C_0$-$C_4$-alkyl, which radicals are unsubstituted or substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulfonyl, aryl-$C_0$-$C_4$-alkoxycarbonyl, aryl, cyano, halogen, heterocyclyl, oxo, trifluoromethoxy, trifluoromethyl or tri-$C_1$-$C_4$-alkylsilyl;
$R^2$ a) is hydrogen; or
  b) is $C_1$-$C_8$-alkyl, $C_3$-$C_8$-cycloalkyl, halogen, carboxy-$C_1$-$C_4$-alkyl, $C_1$-$C_4$-alkoxycarbonyl-$C_1$-$C_4$-alkyl, $C_0$-$C_4$-alkylcarbonyl, aryl-$C_0$-$C_4$-alkyl or unsaturated heterocyclyl-$C_1$-$C_4$-alkyl, which radicals are unsubstituted or substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulfonyl, aryl-$C_0$-$C_4$-alkoxycarbonyl, aryl, cyano, halogen, heterocyclyl, oxo, trifluoromethoxy, trifluoromethyl, or tri-$C_1$-$C_4$-alkylsilyl;
n is a number 0, 1 or 2;
and the salts thereof, preferably the pharmaceutically usable salts thereof,
where, if $R^2$ is hydrogen, $R^1$ is not naphthyl or carbazolyl.

The term aryl stands for an aromatic hydrocarbon radical which generally comprises 5-14, preferably 6-10, carbon atoms and is, for example, phenyl, indenyl, e.g. 2- or 4-indenyl, or naphthyl, e.g. 1- or 2-naphthyl. Aryl having 6-10 carbon atoms is preferred, especially phenyl or 1- or 2-naphthyl. Said radicals may be unsubstituted or substituted one or more times, e.g. once or twice, it being possible for the substituent to be in any position, e.g. in the o, m or p position of the phenyl radical or in the 3 or 4 position of the 1- or 2-naphthyl radical, and it also being possible for a plurality of identical or different substituents to be present.

Aryl-$C_0$-$C_4$-alkyl is, for example, phenyl, naphthyl or benzyl.

The term heterocyclyl stands for a saturated, partially saturated or unsaturated, 4-8-membered, particularly preferably 5-membered, monocyclic ring system, for a saturated, partially saturated or unsaturated, 7-12-membered, particularly preferably 9-10-membered, bicyclic ring system and also for a saturated, partially saturated or unsaturated, 7-12-membered tricyclic ring system, in each case comprising an N, O or S atom in at least one ring, it also being possible for an additional N, O or S atom to be present in one ring. Said radicals may be unsubstituted or substituted one or more times, e.g. once or twice, it also being possible for a plurality of identical or different substituents to be present.

Unsaturated monocyclic heterocyclyl-$C_0$-$C_4$-alkyl is, for example, pyrrolyl, thiophenyl, thiazolyl or oxazolyl.

Unsaturated bicyclic heterocyclyl-$C_0$-$C_4$-alkyl is for example benzofuranyl, benzothiophenyl, indazolyl, indolyl, isoquinolinyl or quinolinyl.

Partially saturated bicyclic heterocyclyl-$C_0$-$C_4$-alkyl is for example 4,5,6,7-tetrahydrobenzofuranyl or 4,5,6,7-tetrahydrobenzothiazolyl.

$C_3$-$C_8$-Cycloalkyl is preferably 3-, 5- or 6-membered cycloalkyl, such as cyclopropyl, cyclopentyl or cyclohexyl.

$C_1$-$C_8$-Alkyl may be straight-chain or branched and/or bridged and is, for example, methyl, ethyl, propyl, isopropyl, butyl, isobutyl, secondary butyl, tertiary butyl, or a pentyl, hexyl or heptyl group.

$C_2$-$C_8$-Alkenyl is, for example, ethenyl, propenyl, isopropenyl, butenyl, isobutenyl, secondary butenyl, tertiary butenyl, or a pentenyl, hexenyl or heptenyl group.

$C_2$-$C_8$-Alkynyl is, for example, ethynyl, propynyl, butynyl, or a pentynyl, hexynyl or heptynyl group.

$C_1$-$C_8$-Alkoxy is, for example, $C_1$-$C_5$-alkoxy such as methoxy, ethoxy, propyloxy, isopropyloxy, butyloxy, isobutyloxy, secondary butyloxy, tertiary butyloxy or pentyloxy, but may also be a hexyloxy or heptyloxy group.

$C_1$-$C_8$-Alkoxycarbonyl is preferably $C_1$-$C_4$-alkoxycarbonyl such as methoxycarbonyl, ethoxycarbonyl, propyloxycarbonyl, isopropyloxycarbonyl, butyloxycarbonyl, isobutyloxycarbonyl, secondary butyloxycarbonyl or tertiary butyloxycarbonyl.

$C_0$-$C_8$-Alkylcarbonyl is, for example, formyl, acetyl, propionyl, propylcarbonyl, isopropylcarbonyl, butylcarbonyl, isobutylcarbonyl, secondary butylcarbonyl or tertiary butylcarbonyl.

$C_1$-$C_4$-Alkoxycarbonyl-$C_1$-$C_4$-alkyl is, for example, methoxycarbonyl- or ethoxycarbonylmethyl, 2-methoxycarbonyl- or 2-ethoxycarbonylethyl, 3-methoxycarbonyl- or 3-ethoxycarbonylpropyl or 4-ethoxycarbonylbutyl.

Halogen is, for example, fluorine, chlorine, bromine or iodine, preferably fluorine, chlorine or bromine.

Carboxy-$C_1$-$C_4$-alkyl is, for example, carboxymethyl, 2-carboxyethyl, 2- or 3-carboxypropyl, 2-carboxy-2-methylpropyl, 2-carboxy-2-ethylbutyl or 4-carboxybutyl, in particular carboxymethyl.

The compound groups mentioned below are not to be regarded as closed; on the contrary, parts of these compound groups may be replaced by one another or by the definitions given above, or be omitted, in a meaningful way, e.g. to replace general by more specific definitions.

Preferred compounds of the formula (I) are compounds of the general formulae

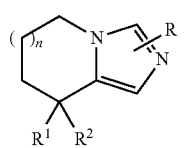

(Ia)

and

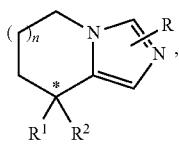

where the meanings of R, $R^1$, $R^2$ and n are as indicated for compounds of the formula (I) and * designates an asymmetric carbon atom.

R is preferably hydrogen or $C_1$-$C_8$-alkyl, particularly preferably hydrogen or methyl.

$R^1$ is preferably aryl or unsaturated heterocyclyl, very particularly preferably optionally mono- or di-substituted benzofuranyl, benzothiophenyl, indazolyl, indolyl, phenyl, pyrrolyl, thiazolyl, thiophenyl or oxazolyl.

$R^2$ is preferably hydrogen, halogen, $C_1$-$C_8$-alkyl or aryl-$C_1$-$C_4$-alkyl.

n is preferably a number 0 or 1. n is particularly preferred the number 1 for compounds of formula (Ib).

Preferred substituents for aryl or unsaturated heterocyclyl are halogen, cyano, trifluoromethoxy, trifluoromethyl, trimethylsilanyl, heterocyclyl or $C_1$-$C_8$-alkylcarbonyl. Very particularly preferred substituents for aryl or unsaturated heterocyclyl are bromine, cyano, thiophenyl, thiazolyl, oxazolyl or acetyl.

A further group of preferred substituents for aryl or unsaturated heterocyclyl, in particular for phenyl, are halogen, trifluoromethoxy, trifluoromethyl, trimethylsilanyl, thiophenyl, methyl, methoxy, heterocyclyl or $C_1$-$C_8$-alkylcarbonyl.

Furthermore, $R^1$ is preferably a di-substituted phenyl substituent or a 3-cyanophenyl substituent.

Particularly preferred compounds of the formula (I) are compounds of the general formulae (Ia) or (Ib) where $R^1$ is aryl, preferably mono- or di-substituted phenyl or unsaturated heterocyclyl, preferably mono- or di-substituted benzofuranyl, benzothiophenyl, indazolyl or indolyl.

With regard to the compounds of formula (I), (Ia) and (Ib) per se (but not to their use or any composition containing said compounds), the compound, wherein R and $R^2$ are H, $R^1$ is p-cyanophenyl and n is 1, is less preferred.

The compounds of the formula (I) which have at least one asymmetric carbon atom can exist in the form of optically pure enantiomers, mixtures of enantiomers or as racemates. Compounds having a second asymmetric carbon atom can exist in the form of optically pure diastereomers, mixtures of diastereomers, diastereomeric racemates, mixtures of diastereomeric racemates or as meso compounds. The invention includes all these forms. Mixtures of enantiomers, racemates, mixtures of diastereomers, diastereomeric racemates or mixtures of diastereomeric racemates can be fractionated by conventional methods, e.g. by racemate resolution, column chromatography, thin-layer chromatography, HPLC and the like.

The compounds of formula (Ib) have at least one asymmetric carbon atom designated as *. Said compounds are to be understood as a single compound having a specific configuration at said asymmetric carbon atom. In case of using a method of preparation leading to racemic compounds, separation of the enantiomers is carried out in a conventional manner, for example using a chiral HPLC-column. Details are found in the examples. Compounds of formula (Ib) according to the current invention show a pronounced aldosterone synthase and/or 11-β-hydroxylase inhibiting activity. Said activity may conveniently be determined by using the cellular assays based on the NCI-H295R human adrenocortical carcinoma cell line as described hereafter. Compounds of formula (Ib) having the opposite configuration at the asymmetric carbon atom designated * show an activity in such a test system which is at least 20-fold, preferably 40-fold, less than the current compounds of formula (Ib).

The term "pharmaceutically usable salts" includes salts with inorganic or organic acids, such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like. Salts of compounds having salt-forming groups are, in particular, acid addition salts, salts with bases or, if a plurality of salt-forming groups is present, optionally also mixed salts or inner salts.

The compounds of the formula (I) can be prepared in a manner analogous to preparation processes disclosed in the literature (scheme).

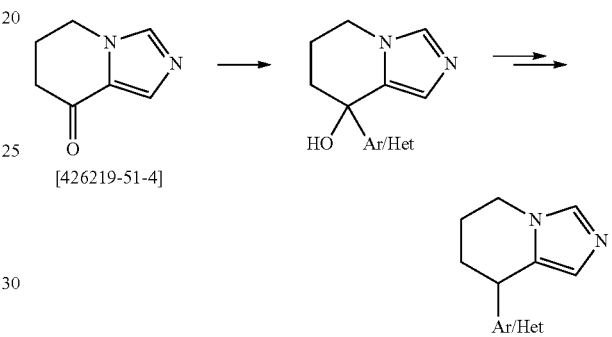

Details of the specific preparation variants can be found in the examples.

The compounds of the formula (I) can also be prepared in optically pure form. Separation into antipodes is possible by methods known per se, either preferably at an early stage of the synthesis by salt formation with an optically active acid such as, for example, (+)- or (−)-mandelic acid and separation of the diastereomeric salts by fractional crystallization or preferably at a rather late stage by derivatization with a chiral auxiliary component such as, for example, (+)- or (−)-camphanyl chloride, and separation of the diastereomeric products by chromatography and/or crystallization and subsequent cleavage of the linkage to the chiral auxiliary. The pure diastereomeric salts and derivatives can be analyzed to determine the absolute configuration of the contained compound using conventional spectroscopic methods, a particularly suitable method being single-crystal X-ray spectroscopy.

Salts are primarily the pharmaceutically usable or nontoxic salts of compounds of the formula (I). Such salts are formed for example by compounds of the formula (I) having an acidic group, e.g. a carboxy or sulpho group, and are, for example, salts thereof with suitable bases, such as nontoxic metal salts derived from metals of group Ia, Ib, IIa and IIb of the Periodic Table of Elements, e.g. alkali metal, in particular lithium, sodium or potassium salts, alkaline earth metal salts, for example magnesium or calcium salts, also zinc salts or ammonium salts, and those salts formed with organic amines such as optionally hydroxy-substituted mono-, di- or trialkylamines, in particular mono-, di- or tri-lower-alkylamines, or with quaternary ammonium bases, e.g. methyl-, ethyl-, diethyl- or triethylamine, mono-, bis- or tris(2-hydroxy-lower-alkyl)amines such as ethanol-, diethanol- or triethanolamine, tris(hydroxymethyl)methylamine or 2-hydroxy-tertiary-butylamine, N,N-di-lower-alkyl-N-(hydroxy-loweralkyl)amine, such as N,N-dimethyl-N-(2-hydroxyethyl) amine, or N-methyl-D-glucamine, or quaternary ammonium hydroxides such as tetrabutylammonium hydroxide.

The compounds of the formula (I) having a basic group, e.g. an amino group, can form acid addition salts, e.g. with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, also amino acids such as, for example, the abovementioned α-amino acids, and methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates) or with other acidic organic compounds such as ascorbic acids. Compounds of the formula (I) having acidic and basic groups can also form inner salts.

Pharmaceutically unsuitable salts can also be used for isolation and purification.

The compounds of the formula (I) also include compounds in which one or more atoms are replaced by their stable, nonradioactive isotopes; for example a hydrogen atom by deuterium.

Prodrug derivatives of the compounds described above are derivatives thereof which on use in vivo release the original compound through a chemical or physiological process. A prodrug may be converted into the original compound for example when a physiological pH is reached or by enzymatic conversion. Examples of possible prodrug derivatives are esters of freely available carboxylic acids, S- and O-acyl derivatives of thiols, alcohols or phenols, where the acyl group is as defined above. Preference is given to pharmaceutically usable ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxy, lower alkoxycarbonyl)-alkyl esters or such as lower α-(alkanoyloxy, alkoxycarbonyl or dialkylaminocarbonyl)-alkyl esters; pivaloyloxymethyl esters and similar esters are conventionally used as such.

Because of the close relatioship between a free compound, a prodrug derivative and a salt compound, a defined compound in this invention also includes its prodrug derivative and salt form where this is possible and appropriate.

Aldosterone is a steroidal hormone which is synthesized in the zona glomerulosa cells of the adrenal cortex by the enzyme aldosterone synthase (CYP11B2). Aldosterone production and secretion is controlled by the adrenocorticotropic hormone (ACTH), angiotensin II, potassium and sodium ions. The primary biological function of aldosterone is to regulate the salt balance, since aldosterone controls the reabsorption of sodium ions from the renal filtrate and the secretion of potassium ions into the renal filtrate. The state of excessive aldosterone secretion, also called hyperaldosteronism, may lead to high blood pressure, hypokalaemia, alkalosis, muscle weakness, polyuria, polydipsia, oedemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The described compounds can be employed for the prevention, for delaying the progression, or for the treatment of states such as hypokalaemia, hypertension, congestive heart failure, acute and, in particular, chronic renal failure, cardiovascular restenosis, atherosclerosis, metabolic syndrome (syndrome X), adiposity (obesity), vasculitis, primary and secondary hyperaldosteronism, proteinuria, nephropathy, diabetic complications such as diabetic nephropathy, myocardial infarction, coronary heart disease, increased collagen formation, fibrosis, vascular and coronary tissue changes (remodelling) secondary to hypertension, endothelial dysfunction and oedemas secondary to cirrhosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is controlled by ACTH. The primary biological function of cortisol is to regulate the production and the availability of carbohydrates for the brain and other metabolically active tissues. Increased cortisol production and secretion is a normal physiological response to stress and leads to the essential mobilization of fats, proteins and carbohydrates to meet an increased demand for energy by the body. Chronically excessive cortisol release describes the condition of Cushing's syndrome. Cushing's syndrome may be produced on the one hand by hypersynthesis of cortisol, which may be generated by an adrenocortical tumour, or be produced on the other hand as the consequence of excessive stimulation of the adrenal cortex by ACTH. The first form is referred to as primary hypercortisolism, and the second form as secondary hypercortisolism. An excessive and persistent cortisol secretion may also accompany a stress response, which may lead to depression, hyperglycemia and to suppression of the immune system.

The chemical compounds described in this invention inhibit the enzyme 11-β-hydroxylase (CYP11B1) and can therefore, due to the inhibition of cortisol synthesis, be employed for the prevention, delaying the progression or treatment of Cushing's syndrome and of the physical and mental consequences of excessive and persistent cortisol secretion in states of stress. Therefore, these compounds may be useful for the treatment and prevention of conditions such as the ectopic adrenocorticotropic (ACTH) hormone syndrome, adrenal incidentaloma, primary pigmented nodular adrenocortical disease (PPNAD) and Carney complex (CNC), anorexia nervosa, chronic alcohol abuse, cigarette smoking, nicotine and cocaine withdrawal, post-traumatic stress disorder, cognitive dysfunction after stroke and cortisol-mediated mineralcorticoid excess.

Inhibition of aldosterone synthase (Cyp11B2), 11-β-hydroxylase (Cyp11B1) and of aromatase (Cyp19) by the compounds described above can be determined by the following in vitro assay:

The cell line NCI-H295R was originally isolated from an adrenocortical carcinoma and has been characterized in the literature through the stimulative secretion of steroid hormones and the presence of the key enzymes necessary for steroidogenesis. These include Cyp11A (cholesterol side-chain cleavage), Cyp11B1 (steroid 11β-hydroxylase), Cyp11B2 (aldosterone synthetase), Cyp17 (steroid 17α-hydroxylase and/or 17,20 lyase), Cyp19 (aromatase), Cyp21B2

(steroid 21-hydroxylase) and 3β-HSD (hydroxysteroid dehydrogenase). The cells have the physiological characteristics of zonally undifferentiated human fetal adrenal cells, with the ability to produce the steroid hormones of each of the three phenotypically distinct zones found in the adult adrenal cortex.

The NCI-295R cells (American Type Culture Collection, ATCC, Rockville, Md., USA) are cultured in Dulbecco's Modified Eagle'Ham F-12 medium (DME/F12) that is supplemented with Ultroser SF serum (Soprachem, Cergy-Saint-Christophe, France) as well as insulin, transferrin, selenit (I-T-S, Becton Dickinson Biosiences, Franklin Lakes, N.J., USA) and antibiotics in 75 $cm^2$ cell culture flasks at a temperature of 37° C. and a 95% air/5% $CO_2$ humidified atmosphere. The cells are subsequently transferred in a 24-well plate and seeded in presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence or absence of cell stimulatory agents. The test compound is added in a concentration range of 0.2 nanomolar to 20 millimolar. Angiotensin-II (at 10 or 100 nanomolar concentration), potassium ions (at 16 millimolar), forskolin (at 10 micromolar) or a combination of two agents may serve as cell-stimulatory agents. The cellular secretion of aldosterone, cortisol, corticosterone and estradiol/estrone into the cell culture medium can be quantitatively assessed with commercially available immuno-assays and specific monoclonal antibodies according to the manufacturer's instructions.

The degree of secretion of a selective steroid is used as a measure of enzyme activity, respectively enzyme inhibition in the presence of absence of a test compound. The dose-dependent enzyme inhibitory activity of a compound is reflected in a inhibition curve that is characterized by an IC50 value. The IC50 values for active test compounds are generated by simple linear regression analysis to establish inhibition curves without data weighing. The inhibition curve is generated by fitting a 4-parameter logistic function to the raw data of the samples using the least squares approach. The function is described as follows:

$$Y=(d-a)/((1+(x/c)^{-b}))+a$$

with:
a=minimum
b=slope
c=IC50
d=maximum
x=inhibitor concentrations

The compounds of the present invention show inhibitory effects in in vitro systems with minimal concentrations of about $10^{-3}$ to about $10^{-10}$ mol/l.

The aldosterone-reducing effect of the compounds described herein can be tested in vivo by the following protocol:

Adult male Sprague Dawley rats, weighing between 125 and 150 grams, are kept, housed singly, under the usual conditions of light and temperature. At 16.00 h on the first day of the experiment, the animals receive a subcutaneous injection of the depot ACTH product in a dose of 1.0 mg/kg of weight (SYNACTEN-Depot, Novartis, Basel, CH). Pilot studies showed that this ACTH dose increased plasma aldosterone and corticosterone significantly by 15-fold and 25-fold respectively over a period of at least 18 hours. At 8.00 h in the morning of the second day, the animals, divided into test groups of 5 animals, receive administration either of water orally or of a compound in a variable dose range of 0.01-10 mg/kg orally by gavage. Two hours later, blood is taken in EDTA-treated Eppendorf vessels. Plasma samples are obtained by centrifugation of the blood and can be stored at −20° C. An alternative method to stimulate the aldosterone secretion consists in subjecting adult male catherized Wistar rats of 250 to 350 grams weight for 48 hours to a low salt diet and 16 hours prior the start of the experiment with an subcutaneous or intraperitoneal application of furosemide at 10 mg/kg. The furosemide application may be repeated 2 hours prior to the start of the experiment. Pilot studies indicated that this treatment results in a 5 to 20 fold increase in plasma aldosterone levels over a period of 12 to 24 hours. The catheters are chronically implanted in the carotid of the animals and allow thus the periodical sampling of up to 0.2 ml of blood using an AccuSampler (DiLab Europe, Lund, Sweden). The experiment starts with the oral administration of test compound in a dose range of 0.01 to 10 mg/kg. The blood sampling with the AccuSampler occurs 1 hour before the administration of test compound and 2, 4, 6, 8, 12, 16 and 24 hours thereafter. The blood samples are anticoagulated with heparin and centrifuged.

The plasma samples derived form both protocols are tested for the steroid content in previously described radioimmunoassays. The reduction in the steroid levels, such as, for example, aldosterone, serves as a measure of the in vivo bioavailability and enzyme inhibiting activity of the compounds described herein.

The reduction of cardiac damage upon inhibition of the aldosterone synthase with the herein described compounds may be evaluated with the following protocol. The protocol corresponds largely to the protocol described in the publication by Rocha et al. (Endocrinology, Vol. 141, pp 3871-3878, 2000). Adult male Wistar rats are housed in individual cages and given 0.9% saline as drinking fluid ad libitum throughout the experiment. Three days later, rats are placed on one of the three dosing protocols. Group I (control group with 8 animals) receives for 14 days the nitric oxide synthase inhibiting agent L-NAME (N-nitro-L-arginine methylester, SIGMA, St. Louis, Mo., USA). On day 11 of L-NAME treatment, an osmotic minipump containing only saline is implanted in each animal subcutaneously. Group II (L-NAME/Ang II with 8 animals) receives L_NAME for 14 days, and on day 11 of L-NAME treatment, an osmotic minipump containing Ang II is implanted in each animal subcutaneaously. Group III (L-NAME/Ang II/test compound with 8 animals) is treated similarly to group II but receives test compound in a daily dose range of 0.2 to 10 mg/kg rat weight. The test compound is dissolved in distilled water and given by oral gavage; whereas groups I and II receive the vehicle without test compound. The experiment is concluded on day 14 of L-NAME treatment L-NAME is administered in 0.9% saline containing drinking water at a concentration of 60 mg/100 ml which results in a daily intake of approximately 60 mg/kg. Angiotensin II is administered via Alzet osmotic mini pumps (model 2001, Alza Corp, Palo Alto, Calif., USA). The minipimp is implanted subcutaneously at the nape of the neck. Angiotensin II (human, 99% peptide purity) is purchased from Sigma Chemical Corp., St Louis, Mo., USA and administered at a dose of 225 ug/kg/day in saline. The concentration of angiotensin II used to fill the pumps is calculated based upon: a) the mean pump rate provided by the manufacturer; b) the body weight of the animals on the day before implantation of the pumps and c) the planned dose. The rats are sacrificed on day 14. Their hearts are removed and sliced through the ventricle/atrium in a "bread-loaf" manner, yielding three samples from the following gross cardiac regions: superior, middle and inferior. The samples are fixed in 10% buffered formalin. Paraffin sections are cut and stained with hematoxyliin/eosin. A single investigator who is blinded to the experimental groups views slides. One slide from each of the three gross cardiac sample regions is analyzed per rat. Cardiac sites (left and right ventricles and the septum) are evaluated separately. The entire section is assessed histologically for the presence of myocardial damage (regardless of the severity) as evidenced by the presence of myocyte necrosis, inflammatory cells, hemorrhages and general tissue disruption. Evaluation of the histological data is made by comparing groups II and III i.e. Angiotensin II with or without test compound. The evaluation of the samples may occur semiquantitatively and can be illustrated with a score table.

The lowering of blood pressure and the reduction of cardiac damage and nephropathy upon inhibition of the aldosterone synthase with the herein described compounds may be evaluated with following protocol. The experiments occur in 4 week old male double transgenic rats (dTGR) that overexpress human angiotensinogen as well as human renin and therefore develop hypertension. Age-paired Sprague-Dawley (SD) rats serve as non-hypertensive control animals. The animals are separated in test groups that receive either test compound or vehicle (control group) for 3-4 weeks. The animals are fed standard chow and get drinking water ad libitum during the whole experiment. The systolic and diastolic blood pressure as well as the heart rate are monitored with implanted telemetric transducers whereby the animals are free and unrestricted to move. The rats are transferred once a week for 24 hours into a metabolic cage in order to measure the 24 hour urinary albumin excretion. The dimensions of the heart (left ventricular mass, end-diastolic diameter and wall thickness, thickness of the septum, shortening fraction) and the diastolic filling are determined by echocardiography at the beginning and the end of the treatment under isofluran anesthesia (M-mode monitoring in the short axis and tissue Doppler representation using a commercial echocardiogram instrument that is equipped with a 15 MHz probe). The animals are sacrificed at the end of the study and the kidneys and heart removed for weighing and immunohistochemical assessment (fibrosis, macrophage/T-cell infiltration, etc.).

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally in tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures permanent release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatin capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatin, disintegrants such as potato starch or crosslinked polyvinylpyrrolidone (PVPP) and lubricants such as stearic acid or magnesium stearate.

Examples of excipients suitable for soft gelatin capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semiliquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

as therapeutic combination in the form of a product or of a kit which is composed of individual components consisting of a compound described herein, in free form or as pharmaceutically usable salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.

as method for combined use, such as, for example, in simultaneous or sequential succession, of a therapeutically effective amount of a compound described herein, in free or in pharmaceutically usable salt form, and of a second active ingredient with blood pressure-lowering, inotropic, antidiabetic, obesity-reducing or lipid-lowering effect.

The compounds described herein and their pharmaceutically usable salts can be used in combination with (i) one or more blood pressure-lowering active ingredients, as such for example:

renin inhibitors such as aliskiren;

angiotensin II receptor blockers such as candesartan, irbesartan, olmesartan, losartan, valsartan, telmisartan etc.;

ACE inhibitors such as quinapril, ramipril, trandolapril, lisinopril, captopril, enalapril etc.;

calcium antagonists such as nifedipine, nicardipine, verapamil, isradipine, nimodipine, amlodipine, felodipine, nisoldipine, diltiazem, fendiline, flunarizine, perhexiline, gallopamil etc.;

diuretics such as hydrochlorthiazide, chlorothiazide, acetazolamide, amiloride, bumetanide, benzthiazide, etacrynic acid, furosemide, indacrinone, metolazone, triamterene, chlortalidone, etc.;

aldosterone receptor blockers such as spironolactone, eplerenone;

endothelin receptor blockers such as bosentan;

phosphodiesterase inhibitors such as amrinone, sildenafil;

direct vasodilators such as dihydralazine, minoxidil, pinacidil, diazoxide, nitroprusside, flosequinan etc., α- and β-receptor blockers such as phentolamine, phenoxybenzamine, prazosin, doxazosin, terazosin, carvedilol, atenolol, metoprolol, nadolol, propranolol, timolol, carteolol etc.;

neutral endopeptidase (NEP) inhibitors;

sympatholytics such as methyldopa, clonidine, guanabenz, reserpine (ii) one or more agents having inotropic activity, as such for example:
cardiac glycosides such as digoxin;
β-receptor stimulators such as dobutamine
thyroid hormone such as thyroxine (iii) one or more agents having antidiabetic activity, as such for example:
insulins such as insulin aspart, insulin human, insulin lispro, insulin glargine and further fast-, medium- and long-acting insulin derivatives and combinations
insulin sensitizers such as rosiglitazone, pioglitazone;
sulphoicnylureas such as glimepiride, chlorpropamide, glipizide, glyburide etc.;
biguanides such as metformin;
glucosidase inhibitors such as acarbose, miglitol;
meglitinides such as repaglinide, nateglinide;

(iv) one or more obesity-reducing ingredients, as such for example:
lipase inhibitors such as orlistate;
appetite suppressants such as sibutramine, phentermine;

(v) one or more lipid-lowering active ingredients, such as, for example,
HMG-CoA reductase inhibitors such as lovastatin, fluvastatin, pravastatin, atorvastatin, simvastatin, rosuvastatin etc.;
fibrate derivatives such as fenofibrate, gemfibrozil etc.;
bile acid-binding active ingredients such as colestipol, colestyramine, colesevelam
cholesterol absorption inhibitors such as ezetimibe
nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The presently described compounds and the pharmaceutically usable salts thereof may find use as combinations with (i) a diagnostic test system, that allows the quantitative determination of the plasma renin concentration (PRC)

(ii) a diagnostic test system, that allows the quantitative determination of the plasma aldosterone concentration (PAC)

(iii) a diagnostic test system, that allows the quantitative determination of the plasma renin activity (PRA)

(iv) a diagnostic test system, that allows the quantitative determination of the plasma aldosterone to renin concentration ratio (ARC)

(v) a diagnostic test system, that allows the quantitative determination of the plasma aldosterone to renin activity ratio (ARR)

(vi) a diagnostic test system, that allows the quantitative determination of the plasma cortisol concentration (PCC)

Such combination of a diagnostic test system and a therapy may be used separately or in preparation with individual components.

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The ratio amounts of solvents to one another is always stated in proportions by volume. Chemical names of final products and intermediates were generated with the aid of the AutoNom 2000 (Automatic Nomenclature) program.

HPLC gradients on Hypersil BDS C-18 (5 μm); column: 4×125 mm

95% water*/5% acetonitrile* to 0% water*/100% acetonitrile* in 10 minutes+2 minutes (1 ml/min).

* contains 0.1% trifluoroacetic acid

The following abbreviations are used:

Rf ratio of the distance migrated by a substance to the distance of the solvent from the starting point in thin-layer chromatography Rt retention time of a substance in HPLC (in minutes)

m.p. melting point (temperature)

EXAMPLE 1

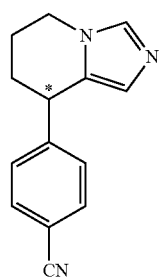 [SMILES: N#Cc1ccc(C2CCCn3cncc32)cc1]

(R or S)-4-(5,6,7,8-Tetrahydro-imidazo[1,5-a]pyridin-8-yl)-benzonitrile

The preparative separation of the enantiomers of (rac)-4-(5,6,7,8-tetrahydro-imidazo[1,5-a]pyridin-8-yl)-benzonitrile is performed with a Chiralpak AD-H column (5 μm, 250×20 mm) using 70:30:0.1 heptane/ethanol/diethylamine as the mobile phase at a flow rate of 50 ml/min. For analytical determinations of the optical purity, a Chiralpak AD-H column (5 μm, 250×4.6 mm) using 70:30:0.1 heptane/ethanol/diethylamine as the mobile phase at a flow rate of 1 ml/min is employed. The second eluting enantiomer is concentrated in vacuo to provide the title compound as a white solid. Rt=15.6.

The starting materials are prepared as follows:
a) (rac)-4-(5,6,7,8-tetrahydro-imidazo[1,5-a]pyridin-8-yl)-benzonitrile A solution of 1.74 mmol of N-tert-Butyl-4-(5,6,7,8-tetrahydro-imidazo[1,5-a]pyridin-8-yl)-benzamide hydrochloride and 1.4 ml of thionyl chloride in 30 ml of chloroform is stirred under reflux for 7 hours. The reaction mixture is cooled to room temperature and evaporated. The residue is taken up in dichloromethane and mixed with saturated aqueous sodium bicarbonate solution. The organic phase is separated off and the aqueous phase is extracted with dichloromethane (2×). The combined organic phases are dried with sodium sulphate and evaporated. Following flash chromatography (SiO$_2$ 60F) of the residue, the resulting solid is stirred in 1:1 diethyl ether/tert-butyl methyl ether, filtered and dried. The title compound is obtained as a cream-colored solid. Rf=0.37 (toluene:methanol=85:15); Rt=4.88 b) N-tert-Butyl-4-(5,6,7,8-tetrahydro-imidazo[1,5-a]pyridin-8-yl)-benzamide hydrochloride A solution of 1.79 mmol of N-tert-Butyl-4-(5,6-dihydro-imidazo[1,5-a]pyridin-8-yl)-benzamide hydrochloride in 8 ml of ethanol is mixed with 270 mg of 10% Pd/C, and the reaction mixture is then hydrogenated at 20-25° C. under atmospheric pressure for 8 hours. The reaction mixture is clarified by filtration and the filtrate is evaporated. The crude title compound is obtained as a brown solid. Rf=0.35 (toluene:methanol=85:15), Rt=5.54.

c) N-tert-Butyl-4-(5,6-dihydro-imidazo[1,5-a]pyridin-8-yl)-benzamide hydrochloride A solution of 1.85 mmol of N-tert-Butyl-4-(8-hydroxy-5,6,7,8-tetrahydro-imidazo[1,5-a]pyridin-8-yl)-benzamide in 6 ml of 2M HCl is stirred at 50° C. for 20 hours. The reaction mixture is cooled to room temperature and cautiously adjusted to pH 8 with saturated aqueous sodium bicarbonate solution. The aqueous phase is extracted with dichloromethane (3×)—the combined organic phases are dried with sodium sulphate and evaporated. The crude title compound is obtained as a grey solid. Rt=5.54.

d) N-tert-Butyl-4-(8-hydroxy-5,6,7,8-tetrahydro-imidazo[1,5-a]pyridin-8-yl)-benzamide 11.6 ml of n-butyllithium (1.6M in hexane) are added dropwise to a solution of 4.250 mmol of 4-bromo-N-tert-butylbenzamide in 200 ml of tetrahydrofuran at −78° C. After 90 minutes, a solution of 6.00 mmol of 6,7-dihydro-5H-imidazo[1,5-a]pyridin-8-one [51907-18-7] in 4 ml of tetrahydrofuran is added dropwise. The reaction mixture is stirred at −78° C. for 1 hour and at room temperature for 2 hours and then quenched with saturated aqueous ammonium chloride solution. The organic phase is separated off and the aqueous phase is extracted with ethyl acetate (2×). The combined organic phases are dried with sodium sulphate and evaporated. The title compound is obtained as a yellow solid from the residue by flash chromatography (SiO$_2$ 60F). Rf=0.16 (dichlormethane:methanol=95:5), Rt=4.96.

The following compounds are prepared in a manner analogous to the processes described in Example 1.
Examples:
2  1-[5-(5,6,7,8-tetrahydroimidazo[1,5-a]pyridin-8-yl)thiazol-2-yl) ethanone starting from 1-[5-(8-hydroxy-5,6,7,8-tetrahydroimidazo[1,5-a]pyridin-8-yl)thiazol-2-yl]ethanone The starting materials are prepared as follows:
a) 1-[5-(8-Hydroxy-5,6,7,8-tetrahydroimidazo[1,5-a]pyridin-8-yl)thiazol-2-yl]ethanone 5 ml of conc. HCl are added dropwise to a solution of 0.31 g of 8-[2-(1,1-dimethoxyethyl)thiazol-5-yl]-5,6,7,8-tetrahydroimidazo[1,5-a]pyridin-8-ol and 20 ml of 1:1 acetone/water at room temperature, and the mixture is stirred for 2 hours. The reaction mixture is evaporated—the residue is mixed with saturated aqueous sodium carbonate solution and extracted with ethyl acetate (3×). The combined organic phases are dried with sodium sulphate and evaporated. The title compound is identified from the residue by flash chromatography (SiO$_2$ 60F) on the basis of the Rf.

8-[2-(1,1-Dimethoxyethyl)thiazol-5-yl]-5,6,7,8-tetrahydroimidazol[1,5-a]pyridin-8-ol 1.63 ml of n-butyllithium (1.6M in hexane) are added dropwise to a solution of 0.41 g of 2-(1,1-dimethoxyethyl)thiazole [200440-13-7] in 15 ml of tetrahydrofuran at −78° C. After 40 minutes, a solution of 0.35 g of 6,7-dihydro-5H-imidazo[1,5-a]pyridin-8-one [426219-51-4] in 10 ml of tetrahydrofuran is added dropwise. The reaction mixture is stirred for 1.5 hours and then poured onto saturated aqueous ammonium chloride solution and extracted with ethyl acetate (3×). The combined organic phases are washed with brine, dried with sodium sulphate and evaporated. The title compound is identified from the residue by flash chromomatography (SiO$_2$ 60F) on the basis of the Rf.

3  8-Benzo[b]thiophen-3-yl-5,6,7,8-tetrahydro-imidazo[1,5-a]pyridine
4  8-Benzofuran-3-yl-5,6,7,8-tetrahydro-imidazo[1,5-a]pyridine
5  8-Benzo[b]thiophen-2-yl-5,6,7,8-tetrahydro-imidazo[1,5-a]pyridine
6  8-(2-Methyl-benzo[b]thiophen-3-yl)-5,6,7,8-tetrahydro-imidazo[1,5-a]pyridine
7  8-(3-Methyl-benzo[b]thiophen-2-yl)-5,6,7,8-tetrahydro-imidazo[1,5-a]pyridine
8  8-Phenyl-5,6,7,8-tetrahydro-imidazo[1,5-a]pyridine
9  8-(4-Fluoro-phenyl)-5,6,7,8-tetrahydro-imidazo[1,5-a]pyridine
10  8-(4-Chloro-phenyl)-5,6,7,8-tetrahydro-imidazo[1,5-a]pyridine
11  8-(4-Bromo-phenyl)-5,6,7,8-tetrahydro-imidazo[1,5-a]pyridine
12  8-(4-Trifluoromethyl-phenyl)-5,6,7,8-tetrahydro-imidazo[1,5-a]pyridine
13  8-(4-Trifluoromethoxy-phenyl)-5,6,7,8-tetrahydro-imidazo[1,5-a]pyridine
14  8-(4-Trimethylsilanyl-phenyl)-5,6,7,8-tetrahydro-imidazo[1,5-a]pyridine
15  8-(3,4-Difluoro-phenyl)-5,6,7,8-tetrahydro-imidazo[1,5-a]pyridine
16  8-(3,4-Dichloro-phenyl)-5,6,7,8-tetrahydro-imidazo[1,5-a]pyridine
17  8-Pyridin-4-yl-5,6,7,8-tetrahydro-imidazo[1,5-a]pyridine
18  2-Fluoro-4-(5,6,7,8-tetrahydro-imidazo[1,5-a]pyridin-8-yl)-benzonitrile
19  2-Methyl-4-(5,6,7,8-tetrahydro-imidazo[1,5-a]pyridin-8-yl)-benzonitrile
20  3-Methyl-4-(5,6,7,8-tetrahydro-imidazo[1,5-a]pyridin-8-yl)-benzonitrile
21  3-(5,6,7,8-Tetrahydro-imidazo[1,5-a]pyridin-8-yl)-benzonitrile
22  2-Fluoro-5-(5,6,7,8-tetrahydro-imidazo[1,5-a]pyridin-8-yl)-benzonitrile
23  8-(1-Methyl-1H-indol-5-yl)-5,6,7,8-tetrahydro-imidazo[1,5-a]pyridine
24  8-(4-Methoxy-phenyl)-5,6,7,8-tetrahydro-imidazo[1,5-a]pyridine
25  8-p-Tolyl-5,6,7,8-tetrahydro-imidazo[1,5-a]pyridine
26  8-(3-Bromo-phenyl)-5,6,7,8-tetrahydro-imidazo[1,5-a]pyridine 27 8-(3-Trifluoromethyl-phenyl)-5,6,7,8-tetrahydro-imidazo[1,5-a]pyridine
28 8-(4-Thiophen-2-yl-phenyl)-5,6,7,8-tetrahydro-imidazo[1,5-a]pyridine
29 8-(3-Thiophen-2-yl-phenyl)-5,6,7,8-tetrahydro-imidazo[1,5-a]pyridine
30 3-Fluoro-4-(5,6,7,8-tetrahydro-imidazo[1,5-a]pyridin-8-yl)-benzonitrile
31 1,3-Dimethyl-5',6',7',8'-tetrahydro-[6,8']bi[imidazo[1,5-a]pyridinyl]
32 8-Benzo[b]thiophen-5-yl-5,6,7,8-tetrahydro-imidazo[1,5-a]pyridine
33 4-(3-Methyl-5,6,7,8-tetrahydro-imidazo[1,5-a]pyridin-8-yl)-benzonitrile 0.63 ml of n-butyllithium (1.6M in hexane) are added dropwise to a solution of 1.0 mmol of 4-(5,6,7,8-tetrahydro-imidazo[1,5-a]pyridin-8-yl)-benzonitrile (Example 1a) in 10 ml of tetrahydrofuran at −40° C. After 15 minutes, a solution of 1.0 mmol methyl iodide in 10 ml of tetrahydrofuran is added dropwise. The reaction mixture is stirred for 1.5 hours and then poured onto saturated aqueous ammonium chloride solution and extracted with ethyl acetate (3×). The combined organic phases are washed with brine, dried with sodium sulphate and evaporated. The title compound is identified from the residue by flash chromatography ($SiO_2$ 60F) on the basis of the Rf.

34 4-(8-Methyl-5,6,7,8-tetrahydro-imidazo[1,5-a]pyridin-8-yl)-benzonitrile 1.4 ml of n-butyllithium (1.6M in hexane) are added dropwise to a solution of 0.33 ml diisopropylamine and 4 ml tetrahydrofuran at 0° C. The resulting solution is then added dropwise to a solution of 2.0 mmol of 4-(5,6,7,8-tetrahydro-imidazo[1.5-a]pyridin-8-yl)-benzonitrile (Example 1a) in 20 ml of tetrahydrofuran at −78° C. After 30 minutes, a solution of 2.0 mmol methyl iodide in 20 ml of tetrahydrofuran is added dropwise. The reaction mixture is stirred for 30 minutes, then warmed to room temperature, poured onto saturated aqueous ammonium chloride solution and extracted with ethyl acetate (3×). The combined organic phases are washed with brine, dried with sodium sulphate and evaporated. The title compound is identified from the residue by flash chromatography ($SiO_2$ 60F) on the basis of the Rf.

The invention claimed is:

1. A compound of the formula

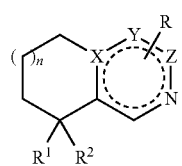

(I)

in which
X is N;
Y is C;
Z is a bond;
R is hydrogen or methyl;
$R^1$ is benzofuranyl, benzothiophenyl, indazolyl, indolyl, pyrrolyl, or oxazolyl optionally mono- or di-substituted with substituents selected from the group consisting of halogen, cyano, trifluoromethoxy, trifluoromethyl, trimethylsilanyl, heterocyclyl and $C_{1-8}$-alkylcarbonyl; or thiazolyl mono- or di-substituted with $C_{1-8}$-alkylcarbonyl
$R^2$ is hydrogen, halogen or $C_1$-$C_8$ alkyl;
n is 1;
or its salt, a pharmaceutically acceptable salt thereof, or compound in which one or more atoms are replaced by their stable, nonradioactive isotopes.

2. The compound according to claim 1, wherein the compound is represented by the formula

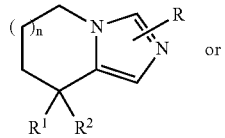

(Ia)

where R, $R^1$, $R^2$ and n are as indicated for compounds of the formula (I) according to claim 1.

3. Method for the prevention, for delaying the progression or for the treatment of pathological states which are caused or partly caused by hyperaldosteronism, where a therapeutically effective amount of a compound of the formula (I) according to claim 1 is used.

4. Method for the prevention, for delaying the progression or for the treatment of pathological states which are caused or partly caused by excessive cortisol release, where a therapeutically effective amount of a compound of the formula (I) according to claim 1 is used.

5. A pharmaceutical product comprising a compound of the formula (I) according to claim 1, and conventional excipients.

6. A pharmaceutical combination in the form of a product or of a kit composed of individual components consisting a) of a compound of the formula (I) according to claim 1, and b) at least one pharmaceutical form whose active ingredient has a blood pressure-lowering, an inotropic, a metabolic or a lipid-lowering effect.

7. Method for the prevention, for delaying the progression or for the treatment of pathological states which are caused or partly caused by hyperaldosteronism, where a therapeutically effective amount of a compound of the formula (Ia) according to claim 2 is used.

8. Method for the prevention, for delaying the progression or for the treatment of pathological states which are caused or partly caused by excessive cortisol release, where a therapeutically effective amount of a compound of the formula (Ia) according to claim 2 is used.

9. A pharmaceutical product comprising a compound of the formula (Ia) according to claim 2, and conventional excipients.

10. A pharmaceutical combination in the form of a product or of a kit composed of individual components consisting a) of a compound of the formula (Ia) according to claim 2, and b) at least one pharmaceutical form whose active ingredient has a blood pressure-lowering, an inotropic, a metabolic or a lipid-lowering effect.

11. A compound selected from the group consisting of:
1-[5-(5,6,7,8-Tetrahydroimidazo[1,5-a]pyridin-8-yl)thiazol-2-yl)ethanone;
8-Benzo[b]thiophen-3-yl-5,6,7,8-tetrahydro-imidazo[1,5-a]pyridine;
8-Benzofuran-3-yl-5,6,7,8-tetrahydro-imidazo[1,5-a]pyridine;
8-Benzo[b]thiophen-2-yl-5,6,7,8-tetrahydro-imidazo[1,5-a]pyridine;
8-(2-Methyl-benzo[b]thiophen-3-yl)-5,6,7,8-tetrahydro-imidazo[1,5-a]pyridine;

8-(3-Methyl-benzo[b]thiophen-2-yl)-5,6,7,8-tetrahydro-imidazo[1,5-a]pyridine;

8-(1-Methyl-1H-indol-5-yl)-5,6,7,8-tetrahydro-imidazo[1,5-a]pyridine;

1,3-Dimethyl-5',6',7',8'-tetrahydro-[6,8']bi[imidazo[1,5-a]pyridinyl]; and

8-Benzo[b]thiophen-5-yl-5,6,7,8-tetrahydro-imidazo[1,5-a]pyridine.

12. The compound according to claim 1, wherein the compound is represented by the formula

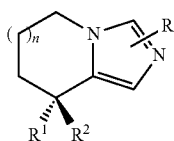

(Ib)

where R, R$^1$, R$^2$ and n are as indicated for compounds of the formula (I) according to claim 1.

13. A pharmaceutical product comprising a compound of the formula (Ib) according to claim 12, and conventional excipients.

14. A pharmaceutical combination in the form of a product or of a kit composed of individual components consisting a) of a compound of the formula (Ib) according to claim 12, and b) at least one pharmaceutical form whose active ingredient has a blood pressure-lowering, an inotropic, a metabolic or a lipid-lowering effect.

15. Method for the prevention, for delaying the progression or for the treatment of pathological states which are caused or partly caused by hyperaldosteronism, where a therapeutically effective amount of a compound of the formula (Ib) according to claim 12 is used.

16. Method for the prevention, for delaying the progression or for the treatment of pathological states which are caused or partly caused by excessive cortisol release, where a therapeutically effective amount of a compound of the formula (Ib) according to claim 12 is used.

* * * * *